United States Patent [19]
Spaulding

[11] Patent Number: 5,330,908
[45] Date of Patent: Jul. 19, 1994

[54] HIGH DENSITY CELL CULTURE SYSTEM

[75] Inventor: Glenn F. Spaulding, Houston, Tex.

[73] Assignee: The United States of America as represented by the Administrator, National Aeronautics and Space Administration, Washington, D.C.

[21] Appl. No.: 996,263

[22] Filed: Dec. 23, 1992

[51] Int. Cl.⁵ .................. C12N 5/02; C12M 1/24; C12M 1/04; C12M 1/10

[52] U.S. Cl. .................. 435/240.24; 435/240.25; 435/286; 435/296; 435/312; 435/313; 435/818

[58] Field of Search .......... 435/240.2, 240.23, 240.24, 435/240.25, 284, 286, 296, 312, 313, 315, 818; 422/102; 215/12.1, DIG. 3; 220/501, 506, 425; 206/524.4

[56] References Cited

U.S. PATENT DOCUMENTS

| | | | |
|---|---|---|---|
| 3,821,087 | 6/1974 | Knazek et al. | 435/313 |
| 4,391,912 | 7/1983 | Yoshida et al. | 435/284 |
| 4,749,654 | 6/1988 | Karrer et al. | 435/240.21 |
| 4,948,728 | 8/1990 | Stephanopoulos et al. | 435/41 |
| 4,962,033 | 10/1990 | Serkes et al. | 435/240.243 |
| 5,015,585 | 5/1991 | Robinson | 435/240.242 |
| 5,026,650 | 6/1991 | Schwarz et al. | 435/286 |
| 5,057,428 | 10/1991 | Mizutani et al. | 435/285 |
| 5,153,131 | 10/1992 | Wolf et al. | 435/240.240 |

FOREIGN PATENT DOCUMENTS 0356785  3/1990  European Pat. Off. ............ 435/284

Primary Examiner—Robert J. Warden
Assistant Examiner—T. A. Trembley
Attorney, Agent, or Firm—Russell E. Schlorff; Guy M. Miller; Edward K. Fein

[57] ABSTRACT

An annular culture vessel for growing mammalian cells is constructed in a one piece integral and annular configuration with an open end which is closed by an endcap. The culture vessel is rotatable about a horizontal axis by use of conventional roller systems commonly used in culture laboratories. The end wall of the endcap has tapered access ports to frictionally and sealingly receive the ends of hypodermic syringes. The syringes permit the introduction of fresh nutrient and withdrawal of spent nutrients. The walls are made of conventional polymeric cell culture material and are subjected to neutron bombardment to form minute gas permeable perforations in the walls.

16 Claims, 2 Drawing Sheets

HIGH DENSITY CELL CULTURE SYSTEM

ORIGIN OF THE INVENTION

The invention described herein was made by an employee of the United States Government and may be manufactured and used by or for the Government of the United States of America for governmental purposes without the payment of any royalties thereon or thereafter.

FIELD OF THE INVENTION

The present invention relates to an improved bio-reactor vessel system which is low cost and universally useful for carrying out mammalian cell and tissue culture processes.

BACKGROUND OF THE INVENTION

Bacterial cell culture processes have been developed for the growth of single cell bacteria, yeast and molds which can be characterized as encased with a tough cell wall. Mammalian cell culture, however, is much more complex because such cells are more delicate and have a more complex nutrient requirement for development. Large scale culture of bacterial type cells is highly developed and such culture techniques are less demanding and are not as difficult to cultivate as mammalian cells. Bacterial cells can be grown in large volumes of liquid medium and can be vigorously agitated without any significant damage. Mammalian cells, on the other hand, cannot withstand excessive turbulent action without damage to the cells and must be provided with a complex nutrient medium to support growth.

In addition, some mammalian cells have a special requirement and must attach themselves to some surface in order to duplicate. Recent technology has been established to grow mammalian cells in horizontally rotating bio-reactors where forced oxygenation is over a sufficient surface area to successfully grow mammalian cells on a large scale. Such devices are disclosed in U.S. Pat. No. 5,026,650, entitled "Horizontally Rotated Cell Culture System with a Coaxial Tubular Oxygenator", and U.S. Pat. No. 5,153,131, entitled "High Aspect Ratio Vessel and Method of Use". These systems function admirably but they are self-contained units and do not adapt for use with existing laboratory equipment and require specific rotational equipment and air pumps.

PRIOR ART

Prior art includes the following patents and, of course, the references cited therein.

U.S. Pat. No. 5,026,650 issued to R. P. Schwarz et. al. on Jun. 25, 1991, relates to a cylindrically formed bioreactor system for mammalian cell growth which is rotated on a central horizontally disposed oxygenating shaft. The shaft has a gas permeable membrane to supply oxygen to a liquid culture medium containing microculture beads and cells. The device has been used successfully to grow high-density cultures of numerous types of previously considered difficult to culture anchorage-dependent mammalian cells.

U.S. Pat. No. 5,153,131 issued to D. A. Wolf, et. al. on Oct. 6, 1992, relates to having the surface area for the oxygenation increased by use of vertical permeable diaphragms. The use of such permeable diaphragms has reduced the distance of the cells from the source of oxygen and has been used successfully for the culturing of suspension type mammalian cells. In both cases, the permeable membrane is not part of the support structure.

U.S. Pat. No. 5,057,428 issued to S. Mizutani et. al. on Oct. 15, 1991, relates to a cylindrical bio-reactor chamber which is rotated about a horizontal axis. There is a cylindrically shaped mesh in chamber which defines inner and outer chambers A piping system conveys oxygen from an air pump into the chamber and a flow path is established to flow return pipes which provide for continuous replenishment of spent medium.

U.S. Pat. No. 5,015,585 issued to J. R. Robinson on May 14, 1991 discloses a bio-reactor construction utilizing a single polymer in a concentric geometric configuration to add durability and reduce complexity.

U.S. Pat. No. 3,821,087 issued to R. A. Knazek et. al. on Jun. 28, 1974 discloses a cell growth system where cells are grown on membranes in a nutrient medium. Nutrient fluids carrying oxygen flow through the vessel and pass through a membrane to contact the cell culture. The fluid is driven by an impeller into the culture vessel. Numerous capillaries are used to distribute oxygen and nutrients over a large area to reduce uneven distribution of resources. There is no rotation of the vessel.

U.S. Pat. No. 4,749,654 issued to D. Karrer et. al on Jun. 7, 1988 relates to a cell growth system using gas permeable membranes and a waste gas removal system. A stirrer is used for agitation. Oxygen flows in through one side of the membrane and carbon dioxide flows out the other.

U.S. Pat. No. 4,948,728 issued to G. Stephanopoules et. al. on Aug. 14, 1990 discloses a porous ceramic material with a plurality of flow passages. A biofilm is in contact with an inner wall and a gas permeable membrane covers the outer wall. An oxygen flow along the outer wall permeates the membrane and ceramic housing to reach biomaterial. Nutrients flow along the inner wall in direct contact with the biofilm.

U.S. Pat. No. 4,962,033 issued to J. M. Serkes et al Oct. 9, 1990 is an example of a cell culture roller bottle which does not have perforated walls.

SUMMARY OF THE PRESENT INVENTION

In the present invention, an annular culture vessel is constructed in a one piece integral and annular configuration with an open end which is closed by an endcap. The culture vessel is rotatable about a horizontal axis by use of conventional roller systems commonly used in culture laboratories. The end wall of the endcap has tapered access ports to frictionally and sealingly receive the ends of hypodermic syringes. The syringes permit the introduction of fresh nutrient and withdrawal of spent nutrients.

In constructing the culture vessel, an annular rigid wall container is formed with an appropriate wall thickness and from a conventional polymeric cell cultural material to the desired annular and rigid one-piece configuration. The walls of the vessel are then subjected to neutron or laser bombardment to form minute gas permeable perforations in the walls. By having both the inner and outer walls oxygen permeable, the surface area available for oxygenation is greatly increased and thus the culture productivity is increased as a direct result of the greater area of oxygenation for the culture.

In the endcap, the separate controlled access entry ports to the interior of the cell culture vessel provide means for sampling, changing or adding fluids or cells to the vessel.

For processing of mammalian cells, the system is sterilized and fresh fluid medium, microcarrier beads, and cells are admitted to completely fill the cell culture vessel so that it has a zero headspace. The oxygen source is passive in that the atmosphere surrounding the walls of the vessel is utilized. This eliminates the need for an air pump. The annular vessel is rotated at a low speed within an incubator so that the circular motion of the fluid medium uniformly suspends the microbeads throughout the annular vessel during the cell growth period. The rotating device for the vessel is a conventional laboratory roller drive means.

The system thus involves rotating a fluid nutrient medium having zero head space where discrete suspension materials disposed in the fluid medium have a same or different density from the density of the fluid nutrient medium. The rotation of the fluid nutrient medium is controlled to place the discrete suspension materials in suspension at spatial locations in the fluid nutrient medium thereby enhancing special co-location relationship with one another. The materials are not subjected to fluid shear forces generated by velocity gradients at the boundary layer at the vessel wall. While rotating the fluid nutrient, oxygen from the surrounding atmosphere is allowed to exchange across the inner and outer walls of the fluid nutrient medium.

It will be appreciated that the culture vessel is simple to construct, low cost and can be widely used by existing laboratories with conventional roller drive units.

DESCRIPTION OF THE PREFERRED EMBODIMENT

Figure 1:
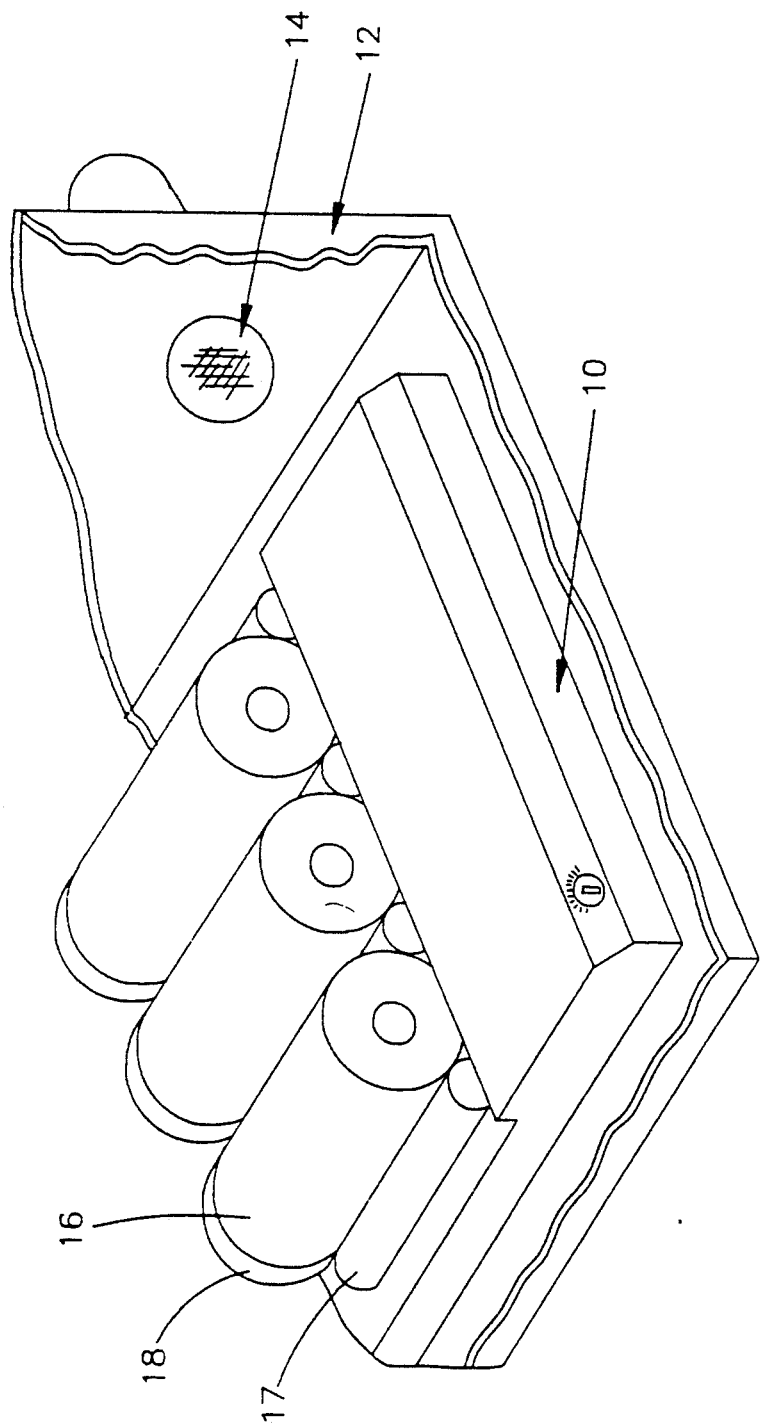
FIG. 1 shows a perspective view of the general organization of the present invention.

Referring now to FIG. 1, the general organization of the present invention is illustrated. A low profile roller unit 10 is shown in an incubator 12 which has a controlled source of heated air 14. If desired, the sources of air and heat can be separate. Roller unit 10 is a commonly used laboratory device for rotating vessels with an outer cylindrical wall about a horizontal axis of the vessel. Thus, drive units are presently readily available and already in use in commercial labs.

The roller unit 10 provides a roller driven mechanism in a well known manner to provide a desired drive speed for the culture vessel. Suitable devices are available from Stoveall Life Science, Inc. of Greensboro, N.C.

As shown in FIG. 1, a culture vessel 16 with a cylindrically formed outer wall is supported and rotated by rollers 17 on the roller unit 10. The vessel 16 is a one piece integral unit with an endcap 18.

Figure 2:
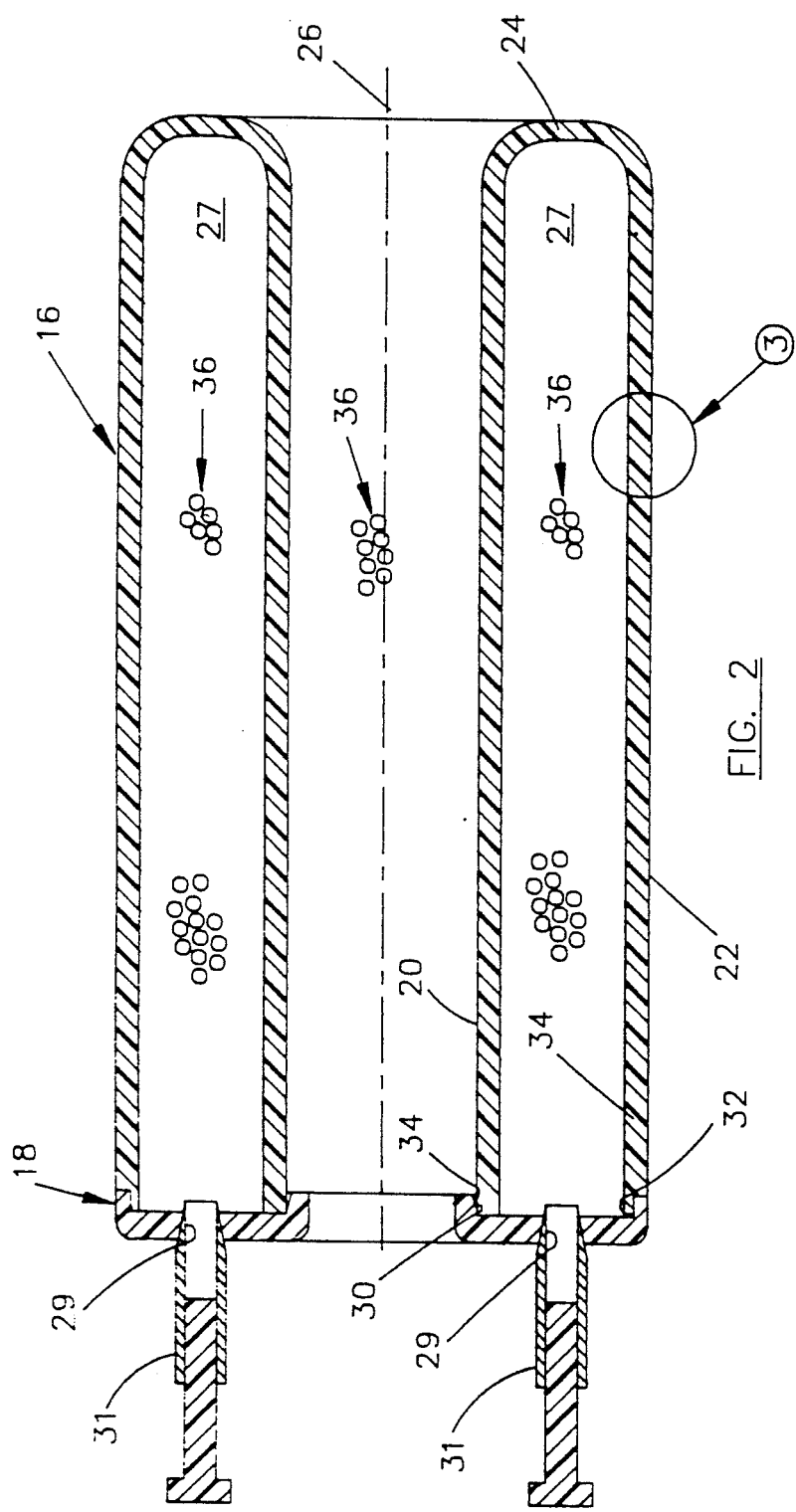
FIG. 2 shows a view in partial cross section through a horizontally rotated cell culture vessel illustrating an application of the present invention.

Referring now to FIG. 2, the culture vessel 16 is annularly shaped with an inner cylindrical wall 20 and an outer cylindrical wall 22 which are connected by a transverse end wall 24. The walls 20 and 22 are concentrically arranged about a longitudinal axis 26 and define an annular chamber 27. An annularly shaped endcap 18 is provided to close the open end of the annular chamber 27. The end cap 18 has an inner cylindrical wall 30 and an outer cylindrical wall 32. The inner surfaces of the walls 30 and 32 can have a beveled end portions 34 to guide the initial coupling of the endcap 18 to the open end of the vessel 16. The fit of the endcap 18 and the open end of the vessel 16 can be a force or snug fit to be liquid tight, or if desired, a sealant can be employed to insure the liquid tight interconnection of the endcap 18 and the vessel 16. As can be appreciated, the endcap 18 and vessel 16 define an annular enclosed chamber 27 about the horizontal axis 26 and when in place, forms a smooth continuation of the wall 22.

In the endcap 18 are portals or openings 29 which sealingly engage the ends of conventional disposable hypodermic syringes 31.

Figure 3:
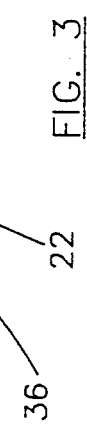
FIG. 3 is a view in cross section taken along the section area designated as "3" in FIG. 2.

The inner wall 20 and the outer wall 22 contain microperforations 36 (see FIG. 3) along their length and about their periphery which are sized relative to the thickness of the walls and the wall material to make the walls gas permeable. Thus, oxygen in the atmosphere can enter the annular chamber from both the inside wall 20 and the outside wall 22 while liquid is retained within the chamber 27.

The culture vessel can be made from a culture compatible material such as polystyrene or polypropylene which can be molded or formed to the desired configuration with a wall configuration which provides a rigid construction yet can be microperforated for gas permeation to the culture within the vessel. As an example of the invention, a sheet of polypropylene having the dimensions of 20 cm×20 cm×1 mm thick may be vacuum formed in steps in a conventional manner in a vacuum form mold to an annular vessel having general dimensions of an inner diameter of 1 cm for the wall 20 and an outside diameter of the wall 22 of 2.5 cm and the axial length being approximately 5 cm and having an approximate volume of 100 ml and the spacing between the inner and outer walls being 5.01 cm or less.

Figure 4:
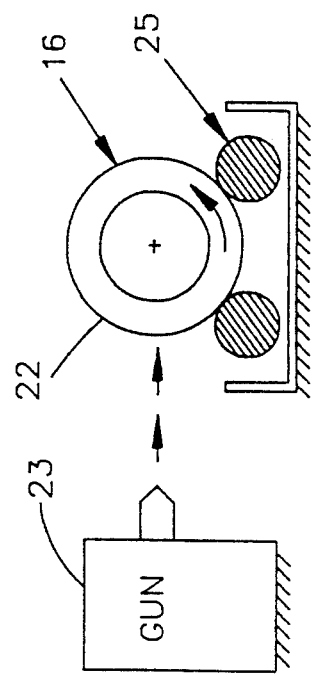
FIG. 4 is a schematic view of a process for perforating the walls of the vessel.

The above unit can be subjected to neutron beam bombardment by rotating the vessel about its longitudinal axis as shown in FIG. 4 and the wall 22 bombarded with a neutron beam from a neutron generator 23 at a direction normal to the axis of the vessel. The neutron generator is moved transversely relative to the axis of the vessel while the vessel is rotated on a roller device 25 which results in the production of holes in the walls 20 and 22 which can have hole diameters of approximately 5 to 20 microns. The hole spacing can be on the order of 50 microns. It will be appreciated that particle, laser, proton or electron beams can be used to perforate the walls.

As an example of use of the culture vessel, Ham's F10 media can be sterilized and placed into the chamber 27 of the culture vessel. The endcap 18 can be securely fastened to the vessel 16. A syringe can be filled with Ham's F10 media and attached to one of the endcap ports 29 so that the chamber can be completely filled with cells with a zero headspace. Such cells are of commercially available origin, being Baby Hamster Kidney (BHK) cells which can be obtained from American Tissue Culture Corporation (ATCC, Rockville, Md.). After cells are injected into the chamber, a new syringe with fresh media can be placed in the port of the endcap. By utilizing another syringe in the other port, any excess air bubbles can be removed according to standard procedures, thereby maintaining a zero head space.

The entire rotating culture vessel with the attached syringes is transferred to a standard incubator and placed upon a commercially available standard roller bottle rotating unit 10. The speed of rotation is adjusted until the cells and beads are normally distributed in suspension throughout the culture vessel 16. As the cells consume culture media products, 50% of the media is replaced with fresh media and a new syringe is placed in the portal opening as previously described for removing air bubbles. The cells are continued on maintenance feeding until they achieved such size as to be useful for additional morphological studies. Functional sizes should range from 100 microns to 1,000 microns. As tissue or cell densities increase, glucose and oxygen requirements increase. The glucose requirements are fulfilled by replacing media with fresh media containing high concentrations of glucose. Oxygen diffusion is enhanced by virtue of increasing the surface area of oxygenation. It has been established that the oxygenation efficiency decreases as a function of the travel distance in the culture media and effectiveness is limited to about one inch or less from the oxygenation surface. Mass transfer and mixing of nutrients is facilitated by movement of suspended cells.

It will be appreciated in the present invention that the core or inner wall and the outer cylinder wall provide both a structural function and an oxygenation function. Use of both the inner and outer walls increase the oxygenation capacity of the rotating oxygenator on the order of 2 to 10-fold as compared to use of a single central core oxygenator member. As will be appreciated, use of both the inner and outer wall surfaces for oxygenation also increases the oxygen capacity of the culture vessel and thus permits both increase cell production and larger cell growths. Additionally, the oxygen effective surface is increased and the spacing between the oxygenation surfaces can be increased while maintaining effective oxygenation of the culture.

As discussed before, the oxygenation is provided by access through perforations sized to admit oxygen yet retain liquid. Due to the inherent hydrophobicity of the structural polymer, large size perforations can be made that allow rapid diffusion of oxygen through the structural element without liquid media leakage. The number of perforations is controlled by the strength of the material and wall thickness required to maintain its rigidity. The size of the perforations can be increased to the extent that the wall material remains non-permeable with respect to the liquid and maintains its structural rigidity.

Alternatively, holes or perforations can be etched into a vessel body as shown in FIG. 4 by utilizing an excitamer laser. An excitamer laser beam can be swept parallel to the horizontal axis while the vessel is rotated. The laser pulses etches holes in the vessel body across and through the outer and inner walls of the vessel. The etched holes can be approximately 100 microns apart and approximately 90 microns in diameter. The criterion for hole size is that the holes should be small enough to prevent the liquid media in the container from leaking or escaping from the container. With polymeric walls having the properties of hydrophobicity, opposing capillary forces prevent culture media from escaping the vessel or container and permits larger diameter pores to be utilized. Consequently, use of a hydrophobic material allows for larger porosity or hole size. Also inherent with larger pore diameters is greater diffusivity and mass transfer of gases through a thicker structural material.

Alternatively, a flat sheet of hydrophobic polymeric material can be etched to make a hole pattern with a selected hole diameter or diameters. The porosity, the spacing and the diameters of the pores or holes can be as previously described. The porous sheet of structural material is then vacuformed to a molded annular shape that approximates the previously described vessel structure. In some instances, there can be an advantage of first creating a flat sheet of perforated material and then molding that sheet into the proper shape.

In an alternate form of the invention, porous plastics (available from Porex Technologies, Fairburn, Ga.) can be injection molded or formed into the vessel shape as previously described. These porous plastics are polymeric and hydrophobic by nature. Once formed, the plastic is both porous and hydrophobic. Examples of available porous plastic are Nylon, Polycarbonate, Polyphthalate carbonate, Polytetrafluoroethylene and Kynar. Other similar polymers can be used. The porous plastics are sintered to the desired structure configuration with the particles of polymer being fused together to obtain a specific porosity and pore diameter. The pore diameter is defined as the orifice diameter; porosity is defined as the number of pores per unit area or the volume of gas per volume of polymer. The pores are generally continuous through a wall but can have a non-linear path. A non-linear path will impart a greater flow restriction to prevent fluid leakage. Consequently, given the hydrophobic nature of the material and a non-linear or tortuous path, the general pore size can be made larger without allowing liquid media to escape. This also permits the plastic to be formed in a thicker wall having greater mechanical and structural integrity. The net result is a good mass transfer of gas from outside the vessel through the walls and, because of increased surface area, there is improved transfer from the air to liquid interface.

If desired, the material can be molded into a variety of shapes and sheet configurations. Since good tensile strength can be maintained, the vessel can be machined into a variety of shapes. Due to the variety of plastics that can be sintered, the vessel can be configured to various cell types and culture requirements, as desired. Also, with sintering injection molding, a cost-effective disposable cell culture unit can be made which is both autoclavable or gamma radiation sterilizable.

It will be apparent to those skilled in the art that various changes may be made in the invention without departing from the spirit and scope thereof and therefore the invention is not limited by that which is disclosed in the drawings and specifications but only as indicated in the appended claims.

I claim:

1. A method for oxygenating mammalian cells in a culture medium comprising the steps of:
   providing an annular culture chamber defined between inner and outer cylindrically formed rigid walls each having gas permeable perforations,
   filling the annular culture chamber with a culture media containing microcarrier beads and mammalian cells to have a zero head space and disposing the annular culture chamber on a roller bottle drive means in an incubator for rotation about a horizontal axis of the annular culture chamber, rotating the annular culture chamber about its horizontal axis at a rotational speed adequate to suspend the microcarrier beads in the culture media for cell growth, oxygenating the culture media through the inner and outer cylindrically formed walls of said annular culture chamber, and adding fresh culture media and withdrawing spent culture media from the annular culture chamber to maintain cell growth during incubation.

2. A method for oxygenating mammalian cells in a culture medium comprising the steps of:

providing an annular culture chamber defined between inner and outer cylindrically formed rigid walls each having has permeable perforations, filling the annular culture chamber with a culture media containing microcarrier beads and mammalian cells to have a zero head space and disposing the annular culture chamber on a roller bottle drive means in an incubator for rotation about a horizontal axis of the annular culture chamber, rotating the annular culture chamber about its horizontal axis at a rotational speed adequate to suspend the microcarrier beads in the culture media for cell growth, passively oxygenating the culture media at atmospheric pressure through the inner and outer cylindrically formed walls of said annular culture chamber, and adding fresh culture media and withdrawing spent culture media from the annular culture chamber to maintain cell growth during incubation.

3. Apparatus for oxygenating mammalian cells in a culture medium comprising:

means defining an annular culture chamber between inner and outer cylindrically formed rigid walls and annular end walls where each inner and outer cylindrically formed wall has gas permeable perforations so that the annular culture chamber can be filled with a culture media containing microcarrier beads and mammalian cells to have a zero head space and can be rotated by a cylinder drive means in an incubator about a horizontal axis of the annular culture chamber and so that the inner cylindrically formed wall has access to the surrounding atmosphere, said outer cylindrically formed wall having sufficient rigidity to support the annular culture chamber and its contents for rotation about its horizontal axis on a roller bottle drive means at a rotational speed adequate to suspend the microcarrier beads in the culture media for cell growth and so that the culture media can be oxygenated by the atmosphere about said annular culture chamber having access through the gas permeable perforations in the inner and outer cylindrically formed walls of said annular culture chamber, and means for adding fresh culture media and for withdrawing spent culture media from the annular culture chamber to maintain cell growth during incubation.

4. The apparatus as set forth in claim 3 wherein said inner and outer cylindrically formed walls of said culture chamber are constructed from a culture compatible plastic material.

5. The apparatus as set forth in claim 4 wherein said culture compatible plastic material is polystyrene.

6. The apparatus as set forth in claim 5 wherein said annular endcap member has openings and said means for adding and for withdrawing are syringe means.

7. The apparatus as set forth in claim 4 wherein said culture compatible plastic material is polypropylene.

8. The apparatus as set forth in claim 4 wherein said annular culture chamber is constructed to be a one piece integral housing member with an annular endcap member.

9. The apparatus as set forth in claim 3 wherein the spacing between said inner cylindrically formed wall and said outer cylindrically formed wall is 5.01 centimeters or less.

10. A rotatable culture chamber for use with conventional laboratory roller devices comprising:

a one piece plastic molded annularly shaped rigid housing having an inner cylindrically shaped wall and an outer cylindrically shaped wall disposed about a common longitudinal axis, an annular transverse end wall between the inner cylindrically shaped wall and the outer cylindrically shaped wall so as to have an open bore through said housing, and an open end, a one piece plastic molded endcap sized for fitted reception on the open end of said inner and outer cylindrically shaped walls to enclose and define an annular culture chamber between the inner and outer cylindrically shaped walls, each of said walls having spaced apart microperforations along the length and about the periphery of said walls for admitting oxygen in the atmosphere to the annular culture chamber while retaining liquid in the annular culture chamber, and openings in the one piece plastic molded endcap sized for fitted reception of a syringe means.

11. The apparatus as set forth in claim 10 wherein said inner and outer cylindrically shaped walls of said culture chamber are constructed from a culture compatible plastic material.

12. The apparatus as set forth in claim 11 wherein said culture compatible plastic material is polystyrene.

13. The apparatus as set forth in claim 11 wherein said culture compatible plastic material is polypropylene.

14. The apparatus as set forth in claim 11 wherein said culture compatible plastic material is polymeric and hydrophobic.

15. The apparatus as set forth in claim 10 wherein the spacing between said cylindrically shaped inner wall and said outer wall is two inches or less.

16. A rotatable culture chamber for use with conventional laboratory roller devices comprising:

a one piece plastic molded annularly shaped rigid housing having an inner cylindrically shaped wall and an outer cylindrically shaped wall disposed about a common longitudinal axis, an annular transverse end wall between the inner cylindrically shaped wall and the outer cylindrically shaped wall so as to have an open bore through said housing, and an open end, a one piece plastic molded endcap sized for fitted reception on the open end of said inner and outer cylindrically shaped walls to enclose and define an annular culture chamber between the inner and outer cylindrically shaped walls, each of said walls having spaced apart non-linear perforations along the length and about the periphery of said walls for admitting oxygen in the atmosphere to the annular culture chamber while retaining liquid in the annular culture chamber, and openings in the one piece plastic molded endcap size for fitted reception of a syringe means.

* * * * *